United States Patent
Hlopick et al.

(10) Patent No.: US 12,350,439 B2
(45) Date of Patent: Jul. 8, 2025

(54) TUNEABLE EXPIRATORY POSITIVE AIRWAY PRESSURE (TEPAP) APPARATUS AND METHOD

(71) Applicant: KONINKLIJKE PHILIPS N.V., Eindhoven (NL)

(72) Inventors: Stephen George Hlopick, Murrysville, PA (US); Richard Daniel Sofranko, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 836 days.

(21) Appl. No.: 17/339,126

(22) Filed: Jun. 4, 2021

(65) Prior Publication Data

US 2021/0379324 A1 Dec. 9, 2021

Related U.S. Application Data

(60) Provisional application No. 63/034,621, filed on Jun. 4, 2020.

(51) Int. Cl.
   *A61M 16/00* (2006.01)
   *A61M 16/08* (2006.01)
   *A61M 16/20* (2006.01)

(52) U.S. Cl.
   CPC ...... *A61M 16/208* (2013.01); *A61M 16/0003* (2014.02); *A61M 16/08* (2013.01)

(58) Field of Classification Search
   None
   See application file for complete search history.

(56) References Cited

U.S. PATENT DOCUMENTS 7,798,148 B2  9/2010 Doshi
7,806,120 B2  10/2010 Loomas
(Continued)

FOREIGN PATENT DOCUMENTS

WO  2009117400 A2  9/2009

OTHER PUBLICATIONS

Kryger MH; Berry RB; Massie CA. Long-term use of a nasal expiratory positive airway pressure (EPAP) device as a treatment for obstructive sleep apnea (OSA) J Clin Sleep Med 2011;7(5):449-453.

(Continued)

*Primary Examiner* — LaToya M Louis
(74) *Attorney, Agent, or Firm* — Michael W. Haas

(57) ABSTRACT

A tuneable expiration positive airway pressure (TEPAP) apparatus (10) comprises an entrainment valve (12) and a module (14), fluidly coupled with an outlet port (60) of the entrainment valve, for tuning an inspiration-to-expiration pressure transition of the breath cycle. The entrainment valve (12) includes a housing (56), an upstream inlet port (58), a downstream outlet port (60), and a valve (62). The valve (62) enables inspiration airflow between an exterior the housing (56) and the inlet port (58) during inspiration and prevents expiration airflow between the inlet port (58) and the exterior of the housing (56) during expiration. The tuning module (14) facilitates at least one rate-of-change in pressure of the inspiration-to-expiration pressure transition that is non-instantaneous. The at least one non-instantaneous rate of change in pressure is selected from among different non-instantaneous rates-of-change in pressure of the inspiration-to-expiration pressure transition.

15 Claims, 10 Drawing Sheets

(56) References Cited

U.S. PATENT DOCUMENTS

| | | |
|---|---|---|
| 7,856,979 B2 | 12/2010 | Doshi |
| 7,987,852 B2 | 8/2011 | Doshi |
| 7,992,563 B2 | 8/2011 | Doshi |
| 9,333,318 B2 | 5/2016 | Cragg |
| 10,086,161 B1 | 10/2018 | Rashidi |
| 2011/0067709 A1 | 3/2011 | Doshi |
| 2014/0109907 A1 | 4/2014 | Doshi |
| 2014/0150801 A1 | 6/2014 | Rusher |
| 2018/0369535 A1 | 12/2018 | Volgyesi |
| 2019/0001187 A1 | 1/2019 | Costella |
| 2019/0015622 A1 | 1/2019 | Ewers |
| 2019/0030274 A1 | 1/2019 | Rashidi |

OTHER PUBLICATIONS

Riaz, M., Certal, V., Nigam, G., Abdullatif, J., Zaghi, S., Kushida, C. A., & Camacho, M. (2015). Nasal Expiratory Positive Airway Pressure Devices (Provent) for OSA: A Systematic Review and Meta-Analysis. Sleep disorders, 2015, 734798. doi:10.1155/2015/734798.

TUNEABLE EXPIRATORY POSITIVE AIRWAY PRESSURE (TEPAP) APPARATUS AND METHOD

CROSS-REFERENCE TO PRIOR APPLICATIONS

This application claims the benefit of U.S. Provisional Application No. 63/034,621 filed Jun. 4, 2020. This application is hereby incorporated by reference herein.

TECHNICAL FIELD

The present embodiments relate generally to Expiratory Positive Airway Pressure (EPAP) apparatus and more particularly, to a tuneable EPAP apparatus and method thereof.

BACKGROUND

Expiratory Positive Airway Pressure presents a novel substitute for Continuous Positive Airway Pressure (CPAP) as the gold standard for the treatment of Obstructive Sleep Apnea. A most well-known provider for EPAP solutions is the company Provent.

EPAP as an alternative to CPAP therapy presents a multitude of self-evident, distinct, and powerful advantages. The advantages include: no electricity required, simplicity, low cost, elimination of blower noise, limited equipment and maintenance (e.g., no hose, machine and limited patient interface), and travel friendly.

While Provent-like EPAP presents a plethora of positive attributes as an alternative for OSA treatment to CPAP, it suffers from non-compliance due to uncomfortable sensations experienced during the expiratory phase of breathing, especially as the patient is falling asleep.

In particular, with respect to Provent-like EPAP inhalation and exhalation patient flow resistance, such a Provent-like EPAP device: (a) suffers from non-compliance due to uncomfortable sensations experienced during exhalation (e.g., like breathing through a straw); (b) is drastically different between IPAP and EPAP conditions; (c) is instantaneous (i.e., the ramp time from IPAP to EPAP is instantaneous); and (d) applicable for mild, moderate, and severe OSA.

At least two journal articles note mixed results on adverse effects of known EPAP devices. "There were no serious device-related adverse events. Device-related adverse events were reported by 42% (17/41) of patients. The most frequent reported events were difficulty exhaling, nasal discomfort, dry mouth, headache, and insomnia." Kryger M H; Berry R B; Massie C A. Long-term use of a nasal expiratory positive airway pressure (EPAP) device as a treatment for obstructive sleep apnea (OSA). J Clin Sleep Med 2011; 7(5):449-453. In addition, "The most commonly reported adverse events were nasal congestion, nasal discomfort, insomnia, headache, dry mouth, dry throat, and discomfort with the device. There were no serious device-related adverse events reported in the clinical trials." Riaz, M., Certal, V., Nigam, G., Abdullatif, J., Zaghi, S., Kushida, C. A., & Camacho, M. (2015). Nasal Expiratory Positive Airway Pressure Devices (Provent) for OSA: A Systematic Review and Meta-Analysis. Sleep disorders, 2015, 734798. doi:10.1155/2015/734798.

However, the known devices for EPAP suffer non-compliance among clinical solutions to the management of Obstructive Sleep Apnea (OSA). It has been shown that this low compliance metric is due to perceived low expiratory comfort levels, as the patient falls asleep. However, EPAP as mechanical resistance to patient flow as an alternative to CPAP therapy presents a multitude of self-evident powerful advantages, if comfort issues can be surmounted.

Accordingly, an improved method and apparatus for overcoming the problems in the art is desired.

SUMMARY

In accordance with one aspect, a method and apparatus for Tuneable Expiratory Positive Airway Pressure (TEPAP) is disclosed which provides "tuned" or "ramped" EPAP from ambient IPAP to the appropriate EPAP setting to equivalently treat obstructive sleep apnea (OSA) similar to that of 5, 10, 20, etc. cm $H_2O$ as can be provided by CPAP, BiPAP, etc., therapy.

In accordance with another aspect, a primary problem addressed by the TEPAP embodiments of the present disclosure is the apparent patient discomfort upon exhalation, during the use of EPAP therapy using known EPAP devices. Accordingly, TEPAP, according to one or more embodiments of the present disclosure, fundamentally provides a solution to low compliance of current EPAP therapy.

In accordance with another aspect, as will be understood from the disclosure herein, TEPAP advantageously provides a supplemental device for the purpose of increasing comfort by using non-anatomical dead-space as a reservoir to buffer immediate EPAP therapy (i.e., to buffer an otherwise immediate rate of change from inspiratory pressure to expiratory pressure for the inspiratory-to-expiratory pressure transition). Additionally, TEPAP dynamically "tunes" or "adjusts" EPAP resistance to patient flow, like a potentiometer, thereby allowing the patient to fall asleep comfortably and be provided therapy naturally over the course of a night or over the duration of needed therapy.

Prior known EPAP devices provide an effective "one-way" resistor to patient flow (i.e., patient air flow), whereas TEPAP according to the embodiments of the present disclosure provides a "one-way" potentiometer to patient flow, as will be better understood from the disclosure herein.

According to one embodiment, a tuneable expiration positive airway pressure apparatus comprises an entrainment valve and an inspiration-to-expiration pressure transition tuning module, fluidly coupled with an outlet port of the entrainment valve, for tuning an inspiration-to-expiration pressure transition of the breath cycle. The entrainment valve includes an entrainment valve housing having an upstream inlet port, a downstream outlet port, and at least one valve. The at least one valve is disposed within a wall of the entrainment valve housing between the inlet port and the outlet port. The at least one valve (i) enables inspiration airflow between an exterior of the entrainment valve housing and the inlet port during an inspiration breathing phase of a breath cycle and (ii) prevents expiration airflow between the inlet port and the exterior of the entrainment valve housing during an expiration breathing phase of the breath cycle. The inspiration-to-expiration pressure transition tuning module facilitates at least one rate-of-change in pressure of the inspiration-to-expiration pressure transition that is non-instantaneous. The at least one non-instantaneous rate of change in pressure is selected from among different non-instantaneous rates-of-change in pressure of the inspiration-to-expiration pressure transition.

According to another embodiment, the inspiration-to-expiration pressure transition tuning module comprises an enclosed volume within a pressure transition housing. In addition, the enclosed volume is fluidly coupled to the entrainment valve outlet port. The enclosed volume further includes at least a first portion having at least one fixed volume size for defining the at least one non-instantaneous rate-of-change in pressure of a transition from inspiration to expiration pressure.

In one embodiment, the pressure transition housing comprises a cylindrical housing. In addition, the inspiration-to-expiration pressure transition tuning module further comprises a piston disposed within the enclosed volume. The piston is displaceable within that enclosed volume between at least a first position and a second position for changing the at least one fixed volume size between a first fixed volume size and a second fixed volume size, different than the first fixed volume size. In a further embodiment, a resilient member is coupled internal to the enclosed volume between the piston and an inner wall of the enclosed volume, wherein the resilient member is configured to adjust a compliance of the enclosed volume.

According to another embodiment, the pressure transition housing comprises (i) a bellows shaped flexible member and (ii) an elastic member. The bellows shaped flexible member forms a portion of the pressure transition housing and defines a boundary portion of the enclosed volume. The elastic member is moveably coupled with the pressure transition housing and displaceable with respect to the enclosed volume between at least a first position and a second position for (i) adjusting the at least one fixed volume size between a first fixed volume size and a second fixed volume size, different than the first fixed volume size, and/or (ii) adjusting a compliance of the bellows shaped flexible member.

In a further embodiment, the pressure transition housing comprises (i) a bellows shaped volume member and (ii) an adjustable elastic member. The bellows shaped volume member comprises a flexibility along at least one axis thereof which defines the enclosed volume. The adjustable elastic member extends between a first position and a second position opposite the first position of the bellows shaped flexible volume member. The adjustable elastic member is adjustable with respect to the enclosed volume between a first tension length and a second tension length for (a) adjusting the at least one fixed volume size between a first fixed volume size and a second fixed volume size, different than the first fixed volume size, and/or (b) adjusting a compliance of the bellows shaped flexible volume member.

According to yet another embodiment, the TEPAP apparatus further comprises a patient interface fluidly coupled to the entrainment valve via the inlet port. In one embodiment, the patient interface and the inspiration-to-expiration pressure transition tuning module are integrally formed. In a still further embodiment, the TEPAP apparatus further comprises a hose fluidly coupled between (i) the entrainment valve outlet port and (ii) the enclosed volume within the pressure transition housing. In one embodiment, the hose and the inspiration-to-expiration pressure transition tuning module are integrally formed. Still further, the TEPAP apparatus can comprise one or more exhalation feature for fluidly coupling an interior of at least one of the entrainment valve and/or the inspiration-to-expiration pressure transition tuning module with an exterior of the at least one of the entrainment valve and/or the inspiration-to-expiration pressure transition tuning module. The one or more exhalation feature are sized to ensure a resistance to a flow of air sufficient to enable an exhalation back pressure during the expiration breathing phase of the breath cycle.

According to another embodiment, a method of tuning expiration positive airway pressure comprises providing an entrainment valve and tuning, via an inspiration-to-expiration pressure transition tuning module fluidly coupled with a downstream outlet port of the entrainment valve, an inspiration-to-expiration pressure transition of the breath cycle. The entrainment valve includes an entrainment valve housing having an upstream inlet port, the downstream outlet port, and at least one valve. The at least one valve is disposed within a wall of the entrainment valve housing between the inlet port and the outlet port for (i) enabling inspiration airflow between an exterior of the entrainment valve housing and the inlet port during an inspiration breathing phase of a breath cycle and (ii) preventing expiration airflow between the inlet port and the exterior of the entrainment valve housing during an expiration breathing phase of the breath cycle. Tuning, via the inspiration-to-expiration pressure transition module, includes facilitating at least one rate-of-change in pressure of the inspiration-to-expiration pressure transition that is non-instantaneous, wherein the at least one non-instantaneous rate of change in pressure is selected from among different non-instantaneous rates-of-change in pressure of the inspiration-to-expiration pressure transition.

In another embodiment, the method includes wherein the inspiration-to-expiration pressure transition tuning module comprises an enclosed volume within a pressure transition housing, and wherein the enclosed volume is fluidly coupled to the entrainment valve outlet port. The enclosed volume further includes at least a first portion having at least one fixed volume size for defining the at least one non-instantaneous rate-of-change in pressure of a transition from inspiration to expiration pressure.

In one embodiment, the pressure transition housing comprises a cylindrical housing, and wherein the inspiration-to-expiration pressure transition tuning module further comprises a piston disposed within the enclosed volume. The piston is displaceable within that enclosed volume between at least a first position and a second position for changing the at least one fixed volume size between a first fixed volume size and a second fixed volume size, different than the first fixed volume size. In addition, the method further comprises coupling a resilient member internal to the enclosed volume between the piston and an inner wall of the enclosed volume, wherein the resilient member is configured to adjust a compliance of the enclosed volume.

In yet another embodiment, the method includes wherein the pressure transition housing comprises (i) a bellows shaped flexible member forming a portion of the pressure transition housing and defining a boundary portion of the enclosed volume, and (ii) an elastic member displaceable with respect to the enclosed volume between at least a first position and a second position for (i) adjusting the at least one fixed volume size between a first fixed volume size and a second fixed volume size, different than the first fixed volume size, and/or (ii) adjusting a compliance of the bellows shaped flexible member.

In a still further embodiment, the method includes wherein the pressure transition housing comprises (i) a bellows shaped volume member having flexibility along at least one axis thereof which defines the enclosed volume, and (ii) an adjustable elastic member extending between a first position and a second position opposite the first position of the bellows shaped flexible volume member, wherein the adjustable elastic member is adjustable with respect to the enclosed volume between a first tension length and a second tension length for (a) adjusting the at least one fixed volume size between a first fixed volume size and a second fixed volume size, different than the first fixed volume size, and/or (b) adjusting a compliance of the bellows shaped flexible volume member. In addition, the method includes fluidly coupling a patient interface to the entrainment valve via the inlet port.

Advantages and benefits will become apparent to those of ordinary skill in the art upon reading and understanding the following detailed description.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

Figure 1A:
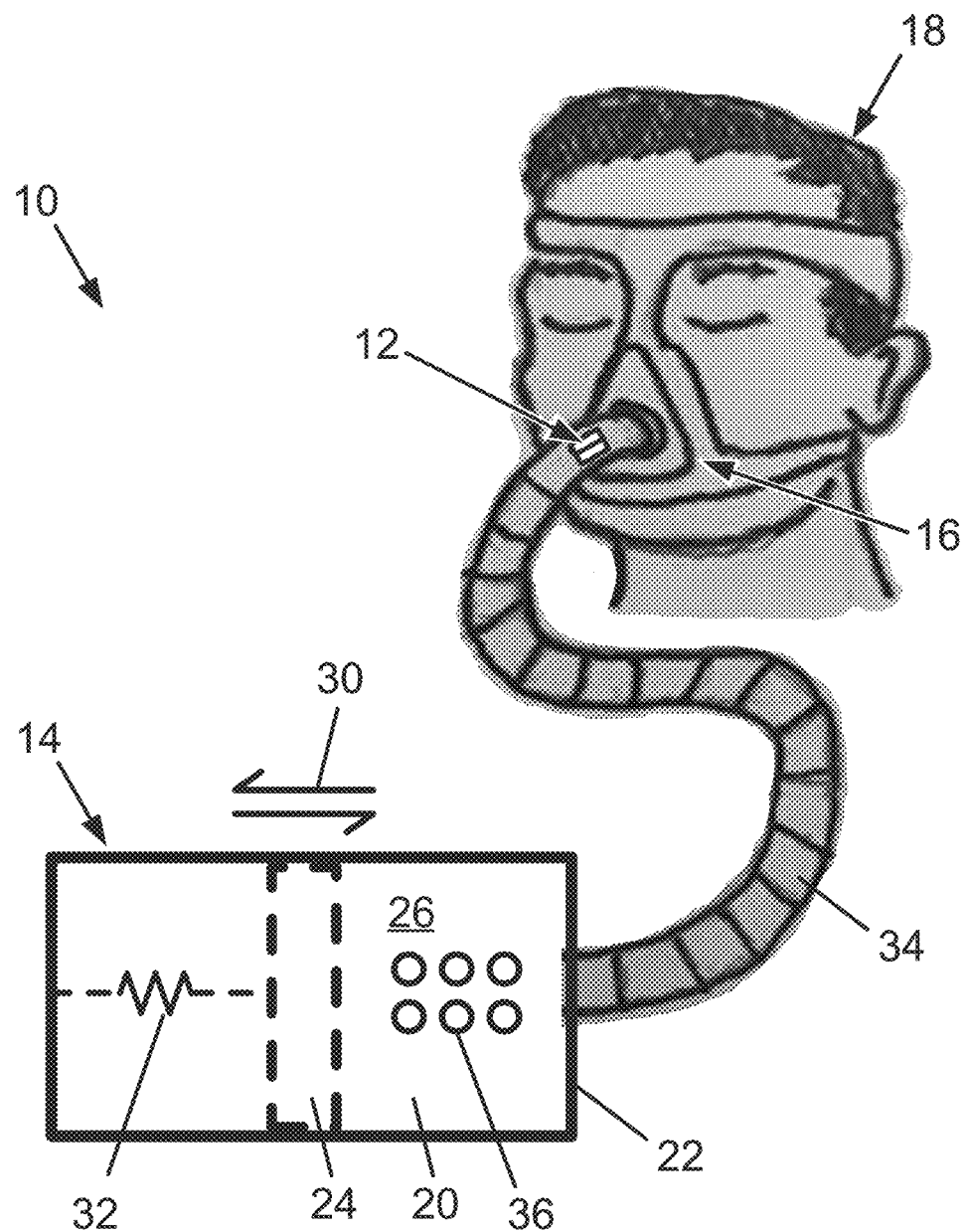
FIGS. 1a and 1b illustrate schematic block representation views of a Tuneable Expiratory Positive Airway Pressure (TEPAP) apparatus according to an embodiment of the present disclosure, further for two of a plurality of different operational settings.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 1B:
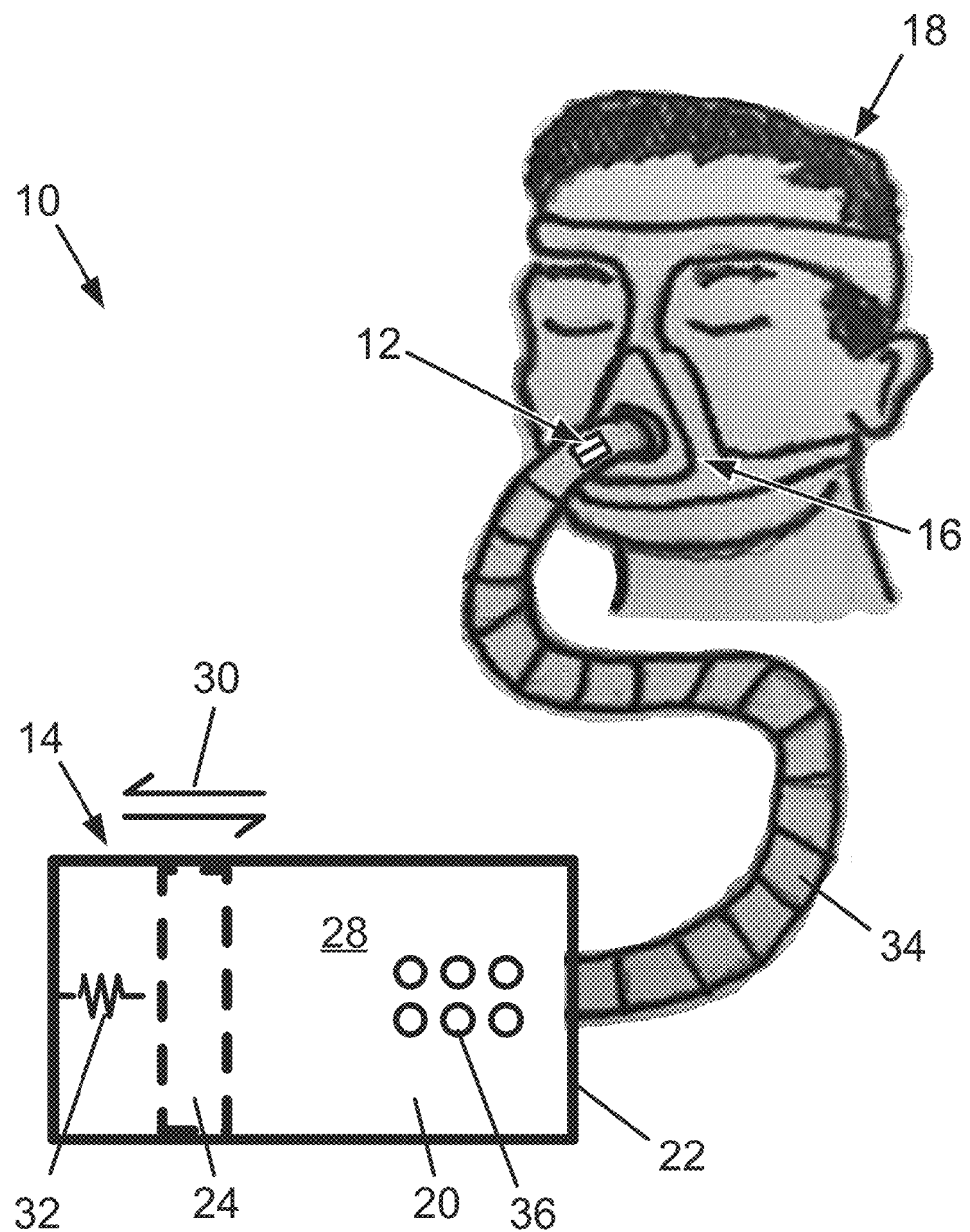

With reference now to the drawings, FIGS. 1a and 1b illustrate schematic block representation views of a Tuneable Expiratory Positive Airway Pressure (TEPAP) apparatus 10 according to an embodiment of the present disclosure. The illustrations in FIGS. 1a and 1b represent two of a plurality of different operational settings, as will further explained herein. The TEPAP apparatus 10 comprises an entrainment valve 12 and an inspiration-to-expiration pressure transition tuning module 14, fluidly coupled with an outlet port of the entrainment valve, for tuning an inspiration-to-expiration pressure transition of the breath cycle. The entrainment valve 12 is fluidly coupled to a patient interface 16, wherein the patient interface is illustrated as being worn by a subject 18. The patient interface 16 can comprise any suitable interface device, such as a mask, as is known in the art and only briefly discussed herein.

As shown, the inspiration-to-expiration pressure transition tuning module 14 comprises an enclosed volume 20 within a pressure transition housing 22. In one embodiment, the pressure transition housing 22 comprises a cylindrical housing, although housings of different geometrical shapes are also contemplated. In addition, the inspiration-to-expiration pressure transition tuning module 14 further comprises a piston 24 disposed within the enclosed volume 20. The piston 24 is displaceable within that enclosed volume 20 between at least a first position (e.g., as shown in FIG. 1a) and a second position (e.g., as shown in FIG. 1b). Additional position displacements of the piston 24 within the enclosed volume 20 are also contemplated, for example, including one or more discrete positions or a plurality of positions, for establishing a given inspiration-to-expiration transition fixed volume size according to the requirements of a given TEPAP implementation.

Displacing the piston 24 between a first position (FIG. 1a) and a second position (FIG. 1b) is carried out for changing at least one fixed volume size of the enclosed volume 20 between a first fixed volume size 26 (FIG. 1a) and a second fixed volume size 28 (FIG. 1*b*), different than the first fixed volume size. Piston 24 can be displaced, as desired, in directions as indicated via arrows 30. Displacing the piston to the right produces a smaller fixed volume size 26, whereas displacing the piston to the left produces a larger fixed volume size 28. A potential for a plurality of various smaller fixed volume and larger fixed volume sizes is contemplated, including a continuously variable volume size from smaller to larger, or vice versa, according to the requirements of a given TEPAP implementation. In particular, the displacement of the piston 24 can be accomplished in a multitude of ways. For example, the piston can be moved, via servo motor (not shown) configured for moving the piston over a period of time. The period of time could be controlled, for example, via a simple electronic timer coupled to the servo motor for controlling one or more movements and/or directions of movement of the servo motor. The one or more selected time(s) of the electronic timer could correspond to various settings of inspiration-to-expiration pressure transition(s) so that a user can initially go to sleep with higher comfort (i.e., a longer EPAP inspiration-to-expiration pressure transition or lower pressure) and thereafter transition to maybe a higher pressure or shorter EPAP inspiration-to-expiration pressure transition, such as required for a given therapy as will be discussed herein below with respect to FIG. 3. In another embodiment, the piston 24 could be manually moved between simple notched settings (now shown) formed within the pressure transition housing 22, wherein each notch corresponds to a given setting of inspiration-to-expiration pressure transition. For example, a user could adjust the piston via the notched settings to set the inspiration-to-expiration pressure transition to the user's personal comfort ("I'm training myself to get to setting 5, but I need to work up to setting 5 from settings 1, 2, 3, and 4 over a period of a couple weeks.").

Referring still to FIGS. 1*a* and 1*b*, in one embodiment, a resilient member 32 is coupled internal to the enclosed volume 20 between the piston 24 and an inner wall of the enclosed volume. In such an arrangement, the resilient member is configured to adjust a compliance of the enclosed volume 20, as will be discussed further herein. In addition, in one embodiment, a hose 34 is fluidly coupled between the entrainment valve 12 and the enclosed volume 20 of the pressure transition housing 22, as will also be further discussed herein.

Lastly, as shown in FIGS. 1*a* and 1*b*, the TEPAP apparatus 10 can optionally comprise one or more exhalation feature 36 for fluidly coupling an interior of at least one of the entrainment valve 12 and/or the inspiration-to-expiration pressure transition tuning module 14 with an exterior of the at least one of the entrainment valve and/or the inspiration-to-expiration pressure transition tuning module. The one or more exhalation feature 36 can comprise apertures and/or holes sized to ensure a resistance to a flow of air sufficient to enable an exhalation back pressure within the air flow circuit of the apparatus 10 during the expiration breathing phase of the breath cycle. In one embodiment, one or more exhalation features, generally indicated via reference numeral 36, are disposed on the pressure transition housing 22. Other locations for the optional exhalation features are also possible.

Figure 2:
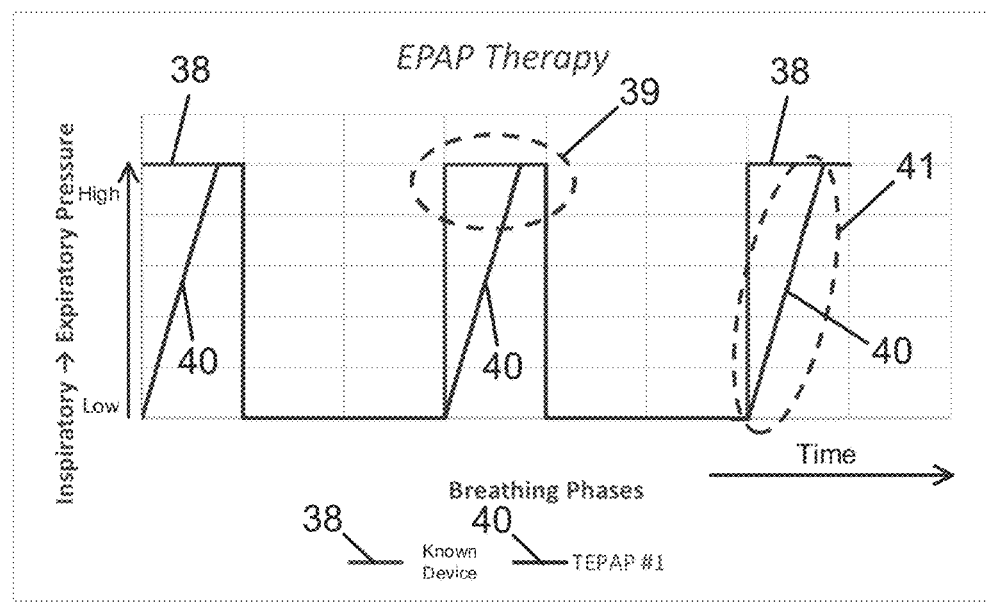
FIG. 2 is a graphical representation view of inspiratory-to-expiratory pressure transitions per breathing cycles as a function of time for a known EPAP device compared with a TEPAP apparatus according to an embodiment of the present disclosure.

With reference now to FIG. 2, there is shown a graphical representation view of inspiratory-to-expiratory pressure transitions (vertical axis, low inspiratory to high expiratory pressure) per breathing cycles or phases (horizontal axis, inspiration and expiration phases) as a function of time for a known EPAP device compared with a TEPAP apparatus according to an embodiment of the present disclosure. In particular, the graphical representation of FIG. 2 illustrates a therapy 38 via a known EPAP device in which the known EPAP device provides instantaneous EPAP, i.e., an instantaneous rate-of-change in pressure of the inspiration-to-expiration pressure transition (i.e., equivalent to 5, 10, 12 $H_2O$ cm). That is, the known EPAP device supplies therapy across a whole expiratory phase, indicated via reference numeral 39, throughout an entire sleep cycle. In contrast, the TEPAP apparatus 10 functions differently than the traditional EPAP therapy. That is, the TEPAP apparatus 10 ramps an equivalent therapy pressure over the expiratory phase of the breath. As indicated by reference numeral 41 in FIG. 2, the TEPAP apparatus 10 provides a linear ramped expiratory resistance, during the indicated breathing phase.

Figure 3:
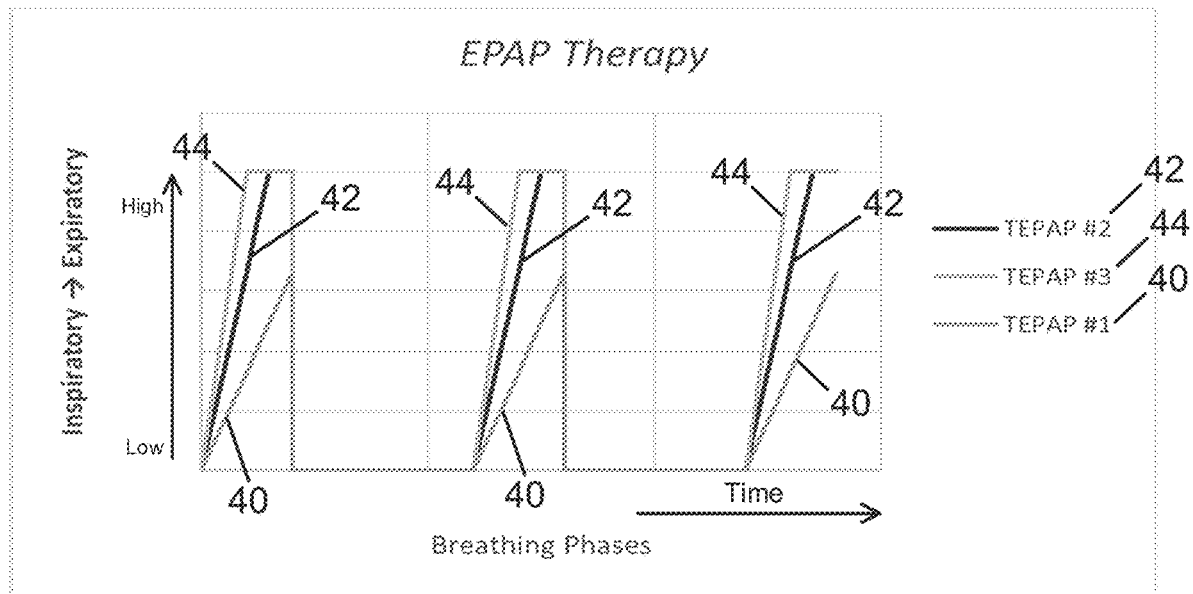
FIG. 3 is a graphical representation view of inspiratory-to-expiratory pressure transitions per breathing cycles as a function of time for three different rates of change in transition of inspiratory-to-expiratory pressure with the TEPAP apparatus according to an embodiment of the present disclosure.

With reference now to FIG. 3, there is shown a graphical representation view of inspiratory-to-expiratory pressure transitions per breathing cycles as a function of time for three different rates of change (indicated as TEPAP #1, TEPAP #2 and TEPAP #3) in transition of inspiratory-to-expiratory pressure with the TEPAP apparatus 10. The TEPAP apparatus 10 can be configured to produce different TEPAP ramp times that are achievable via the same device, for example, via a corresponding number of different settings of fixed volume sizes (e.g., 26, 28, etc.) of the enclosed volume 20 within the pressure transition housing 22. In FIG. 3, only three different ramp times are shown, however, any number of different ramp times may be provided according to the particular requirements of a given overall TEPAP therapy.

In other words, the TEPAP apparatus 10 can be set to different enclosed volume configurations, e.g., TEPAP #1, TEPAP #2 and TEPAP #3, over a given period of therapy (e.g., through the night time during sleep) to increase therapy time and pressure during expiratory breathing. Different TEPAP ramp times can be achieved via the apparatus 10 to achieve necessary levels of comfort through the night. The EPAP pressure can be low at start up and be gradually changed to higher pressure and longer duration of EPAP. Setting of the different enclosed volume configurations can be accomplished as discussed herein with respect to FIGS. 1*a*, 1*b*, 7*a*, 7*b*, 8*a*, and 8*b*.

Referring still to FIG. 3, the three different therapies can be provided via TEPAP #1, TEPAP #2 and TEPAP #3 which are indicated by reference numerals 40, 42 and 44, respectively. Thus, at the beginning of sleep, a therapy setting TEPAP #1 can provide a gentle transition or rate of change in pressure of the inspiratory-to-expiratory transition (i.e., a non-instantaneous transition), which could be followed by TEPAP #2 and/or TEPAP #3, as appropriate, during expiratory breathing of subsequent sleep. The use of linear slopes for the TEPAP rate of change in pressure of the inspiratory-to-expiratory transition is only one example. Other embodiments may utilize slopes that could include exponential, polynomial decay, etc.

Figure 4:
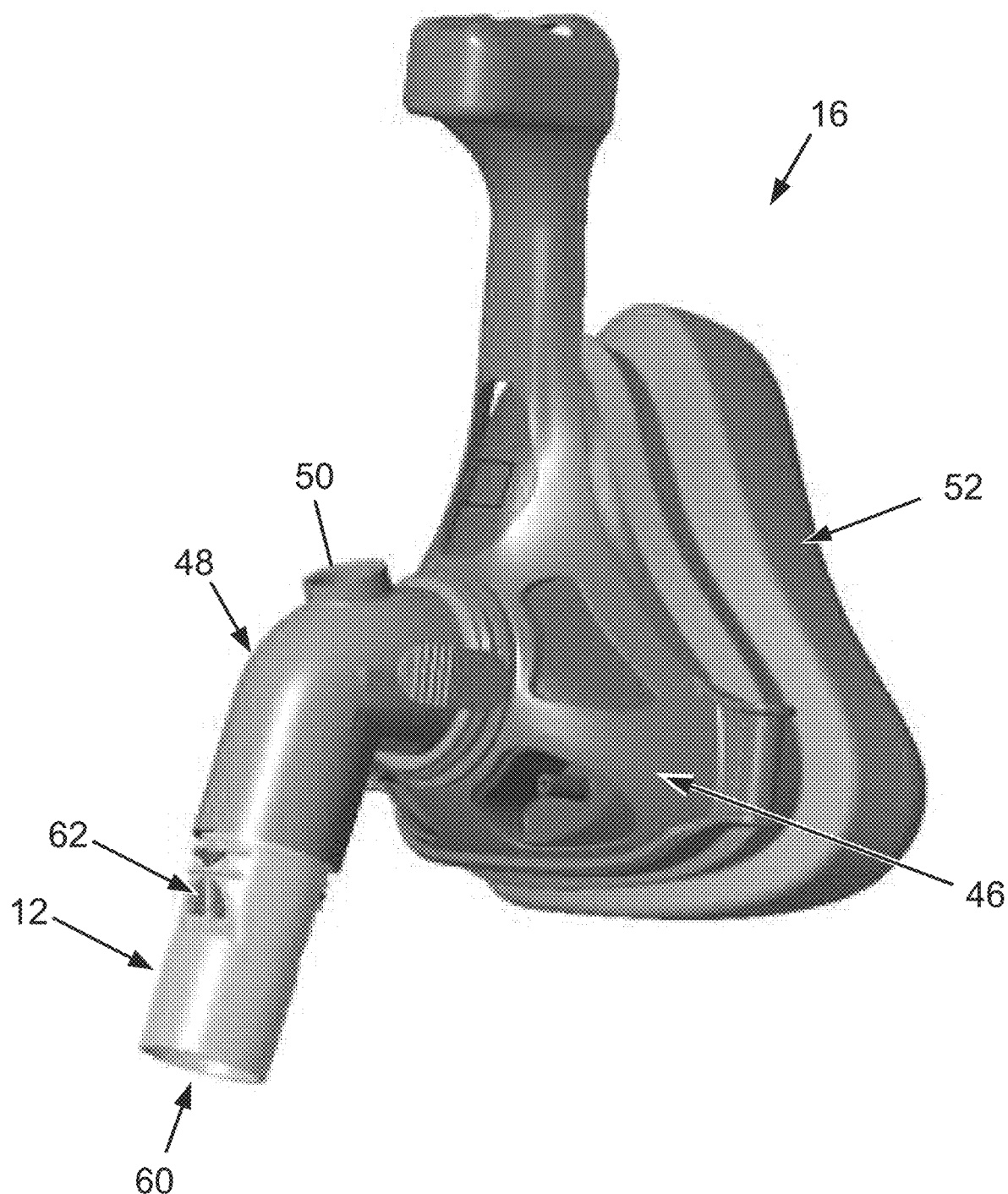
FIG. 4 is a perspective view of a patient interface mask configured to receive an entrainment valve of the TEPAP apparatus according to an embodiment of the present disclosure.

With reference now to FIG. 4, a perspective view of a patient interface mask 16 configured to receive an entrainment valve 12 of the TEPAP apparatus 10 according to an embodiment of the present disclosure is shown. The patient interface 16 can comprise any suitable patient interface mask for covering the nose and mouth (or a nasal mask for covering the nose alone) of a subject 18. The patient interface 16 can comprise a frame 46 with corresponding strap (not shown), an elbow 48, an optional nebulizer port 50 (which may or may not be present), and a soft resilient sealing member 52. In the event the elbow 48 includes a nebulizer port 50, a plug (not shown) may be provided for sealing the nebulizer port 50 in the absence of a nebulizer.

Figure 5:
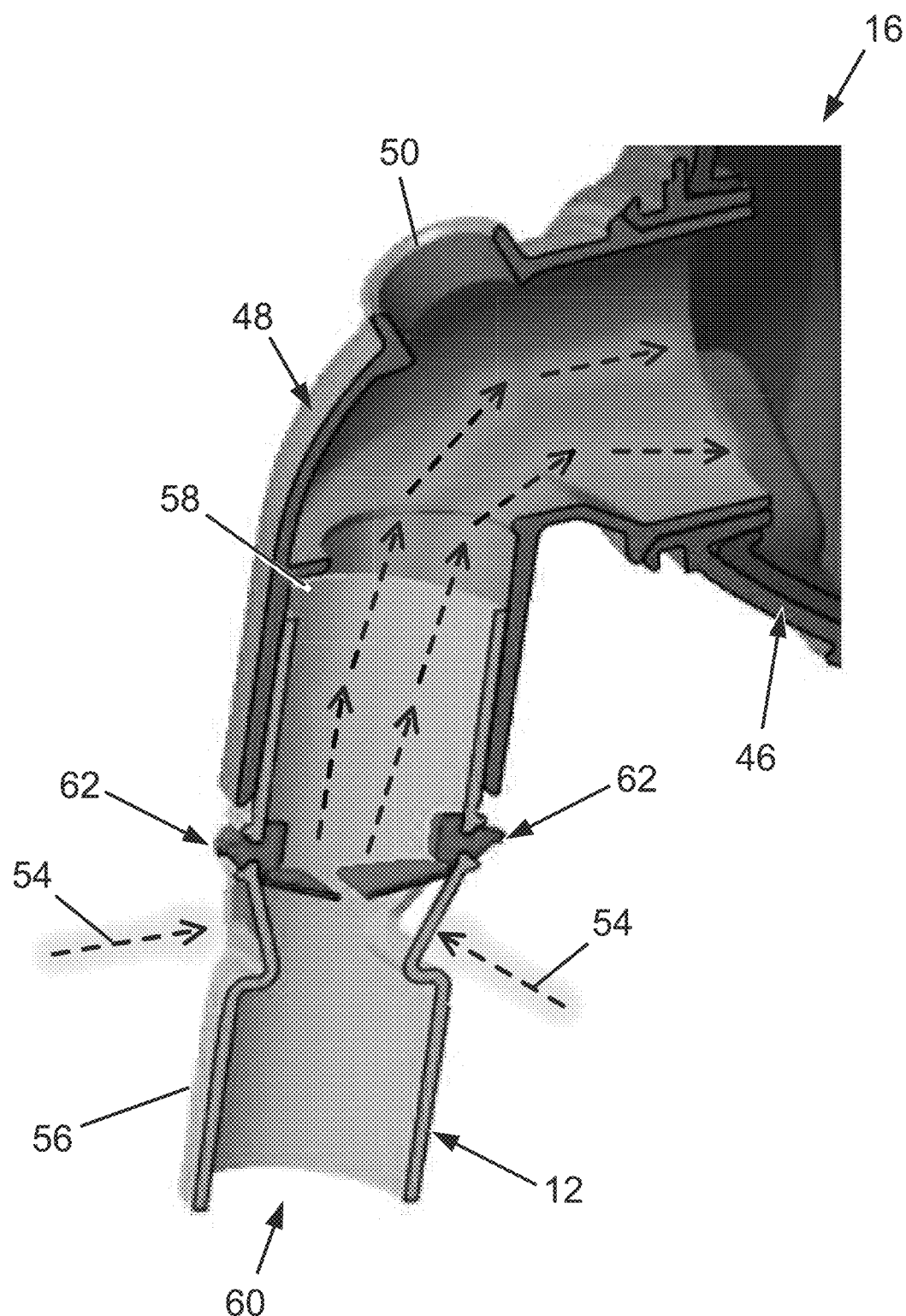
FIG. 5 is a cut-away perspective view of the entrainment valve shown in FIG. 4, illustrating flow of air during an inspiration phase of a breathing cycle with the TEPAP apparatus according to an embodiment of the present disclosure.
Figure 6:
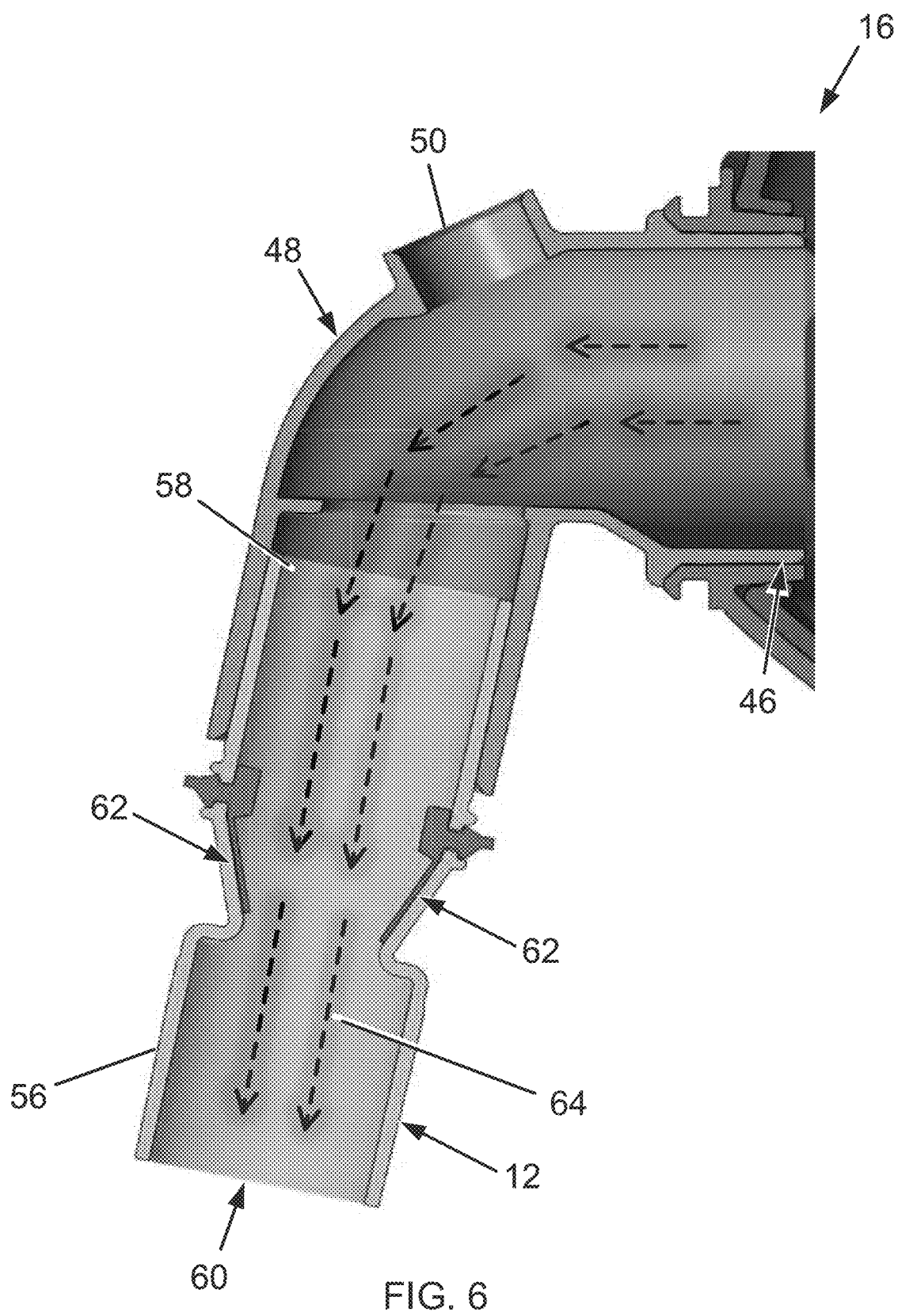
FIG. 6 is a cut-away perspective view of the entrainment valve shown in FIG. 4, illustrating flow of air during an expiration phase of a breathing cycle with the TEPAP apparatus according to an embodiment of the present disclosure.

In FIG. 5, a cut-away perspective view of the entrainment valve 12 of FIG. 4 is shown that illustrates a flow of air 54 during an inspiration phase of a breathing cycle with the TEPAP apparatus according to an embodiment of the present disclosure. The entrainment valve 12 includes an entrainment valve housing 56 having an upstream inlet port 58, a downstream outlet port 60, and at least one valve 62 (two valves are shown in FIG. 5). The at least one valve 62 is disposed within a wall of the entrainment valve housing 56 between the inlet port 58 and the outlet port 60. The at least one valve (i) enables inspiration airflow 54 between an exterior of the entrainment valve housing 56 and the inlet port 58 during an inspiration breathing phase of a breath cycle and (ii) prevents expiration airflow 64 (FIG. 6) between the inlet port 58 and the exterior of the entrainment valve housing 56 during an expiration breathing phase of the breath cycle. FIG. 6 is a cut-away perspective view of the entrainment valve shown in FIG. 4, illustrating flow of air during an expiration phase of a breathing cycle with the TEPAP apparatus according to an embodiment of the present disclosure.

Referring back to FIGS. 1a, 1b, and 4-6, the TEPAP apparatus 10 can further comprise the patient interface 16 fluidly coupled to the entrainment valve 12 via the inlet port 58. In one embodiment, the patient interface 16 and the inspiration-to-expiration pressure transition tuning module 14 are integrally formed. In a still further embodiment, the TEPAP apparatus 10 further comprises a hose 34 fluidly coupled between (i) the entrainment valve outlet port 60 and (ii) the enclosed volume 20 within the pressure transition housing 22. In one embodiment, the hose 34 and the inspiration-to-expiration pressure transition tuning module 14 are integrally formed.

The inspiration-to-expiration pressure transition tuning module 14 advantageously facilitates at least one rate-of-change in pressure of the inspiration-to-expiration pressure transition that is non-instantaneous. The at least one non-instantaneous rate of change in pressure can be selected from among different non-instantaneous rates-of-change in pressure of the inspiration-to-expiration pressure transition.

In addition, the enclosed volume 20 is fluidly coupled to the entrainment valve outlet port 60. The enclosed volume 20 further includes at least a first portion having at least one fixed volume size 26 for defining the at least one non-instantaneous rate-of-change in pressure of a transition from inspiration to expiration pressure.

Figure 7A:
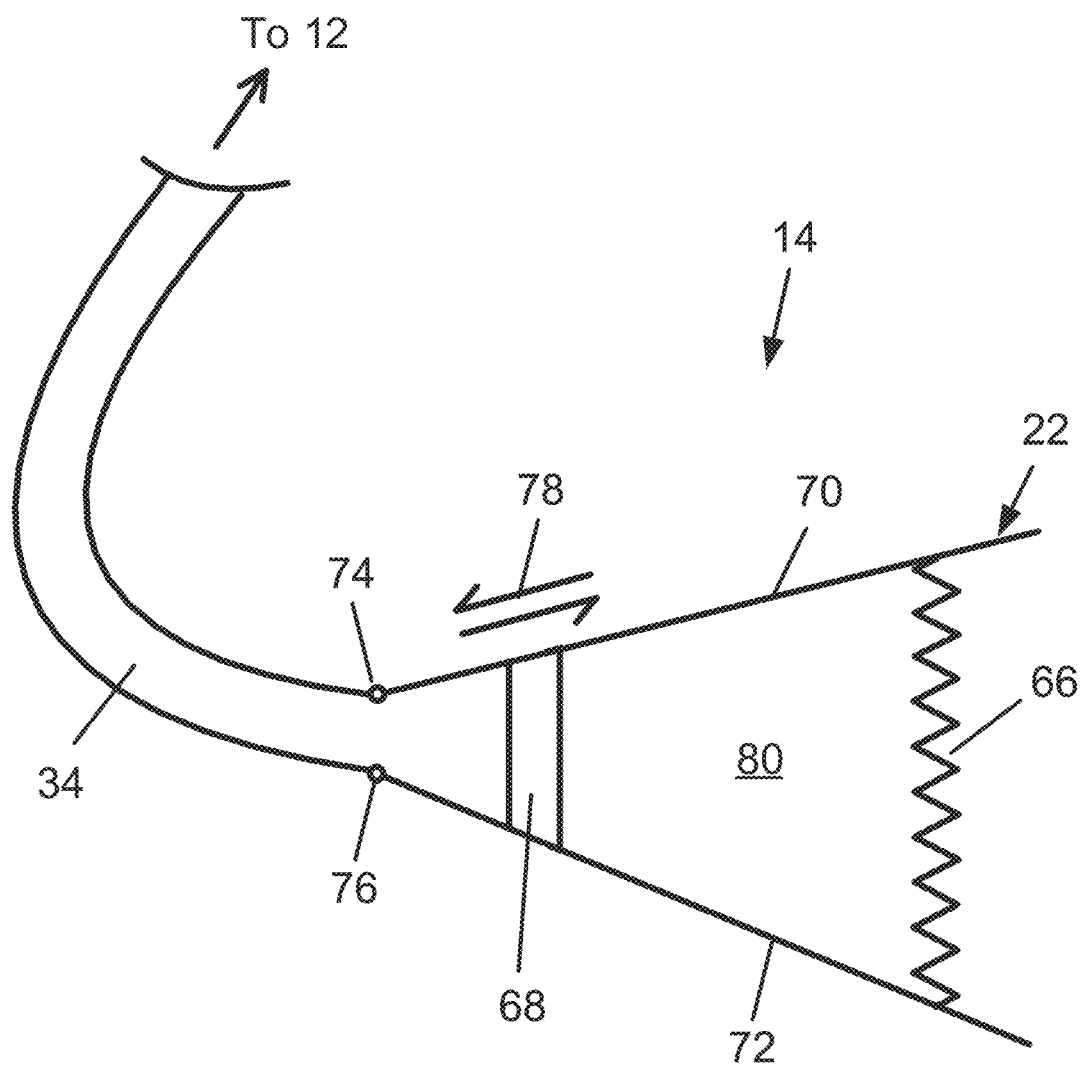
FIGS. 7a and 7b illustrate schematic block representation views of a portion of the TEPAP apparatus according to another embodiment of the present disclosure, further for two of a plurality of different operational settings.
Figure 7B:
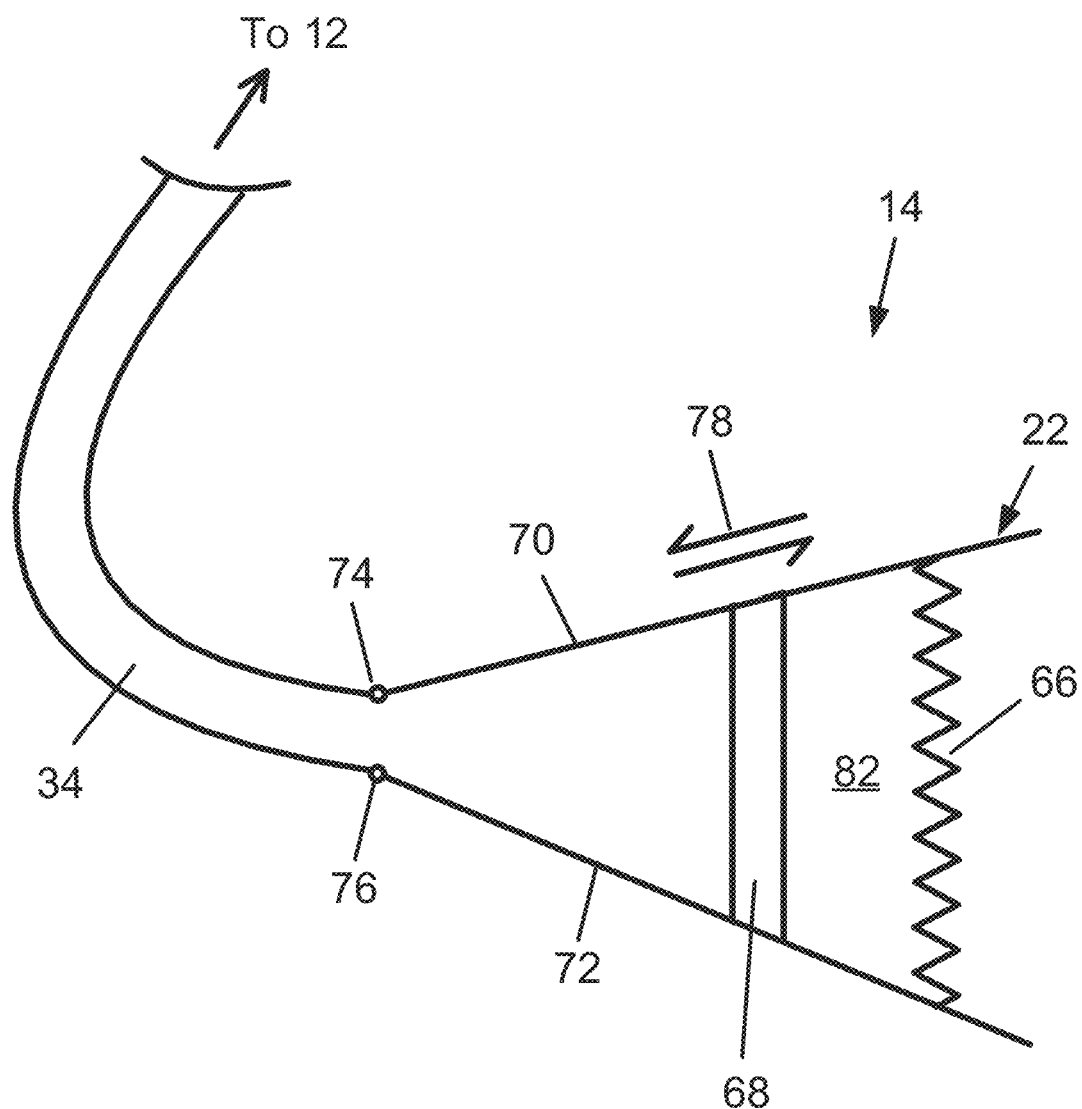

Referring now to FIGS. 7a and 7b, illustrated are schematic block representation views of a portion of the TEPAP apparatus 10 according to another embodiment of the present disclosure, further for two of a plurality of different operational settings. The embodiment of FIGS. 7a and 7b are similar to the embodiment of FIGS. 1a and 1b, with the following differences. In particular, the pressure transition housing 22 comprises (i) a bellows shaped flexible member 66 and (ii) an elastic member 68.

The pressure transition housing 22 may further comprise top and bottom plates 70, 72 which are coupled at respective sides and distal ends thereof to the bellows shaped flexible member 66. At the proximal end, the top and bottom plates 70, 72 are hingedly coupled, e.g., at hinge portions 74, 76 to a proximal end of hose 34. The distal end of hose 34 is coupled to the outlet port of the entrainment valve 12. The pressure transition housing 22 included enclosed volume 20. The bellows shaped flexible member 66 forms a portion of the pressure transition housing 22 and defines a boundary portion of the enclosed volume 20. The elastic member 60 is moveably coupled with the pressure transition housing 22 and displaceable, in directions as indicated via arrows 78, with respect to the enclosed volume 20 between at least a first position and a second position for (i) adjusting the at least one fixed volume size between a first fixed volume size 80 and a second fixed volume size 82, different than the first fixed volume size, and/or (ii) adjusting a compliance of the bellows shaped flexible member 66.

Figure 8A:
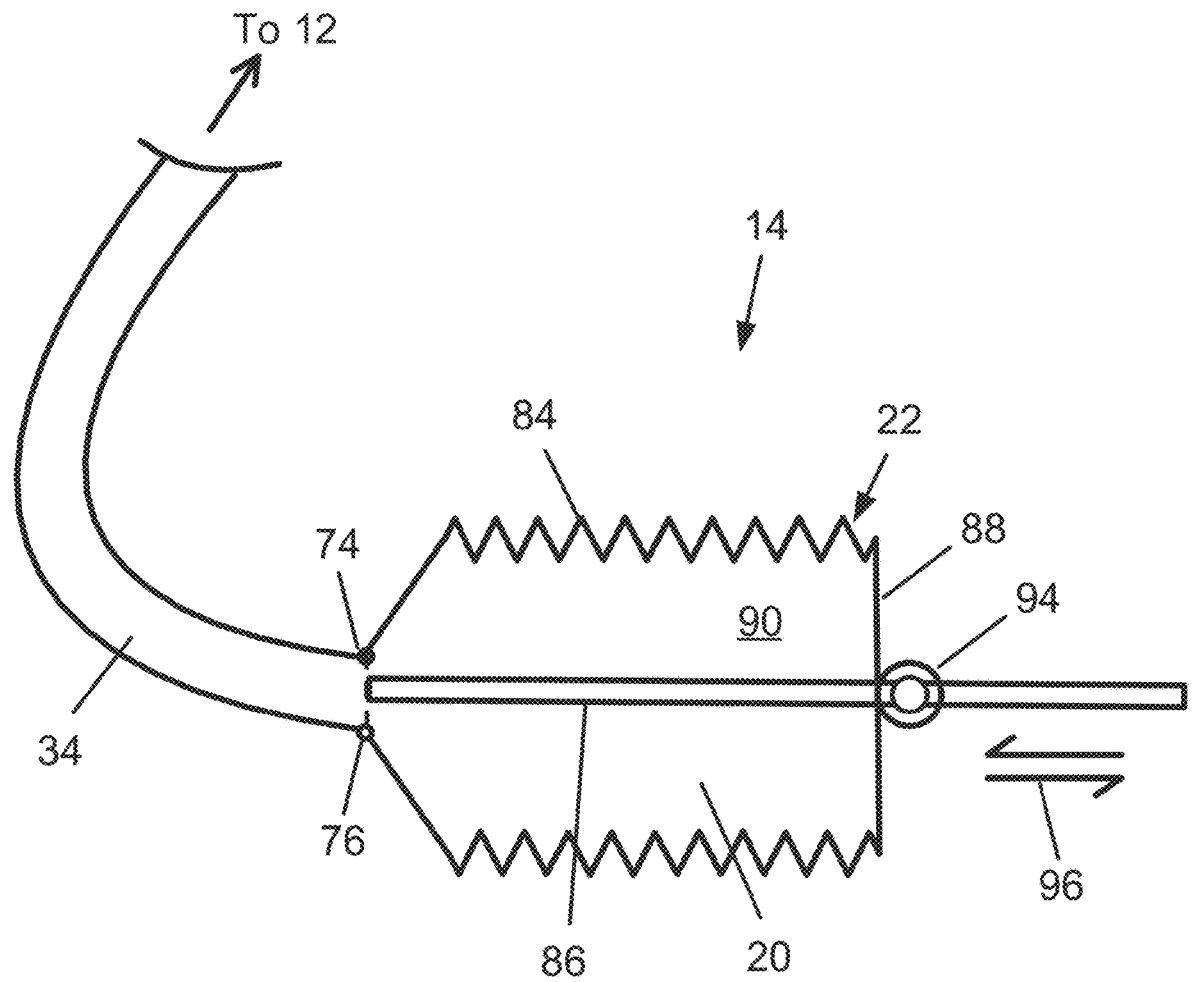
FIGS. 8a and 8b illustrate schematic block representation views of a portion of the TEPAP apparatus according to yet another embodiment of the present disclosure, further for two of a plurality of different operational settings.
Figure 8B:
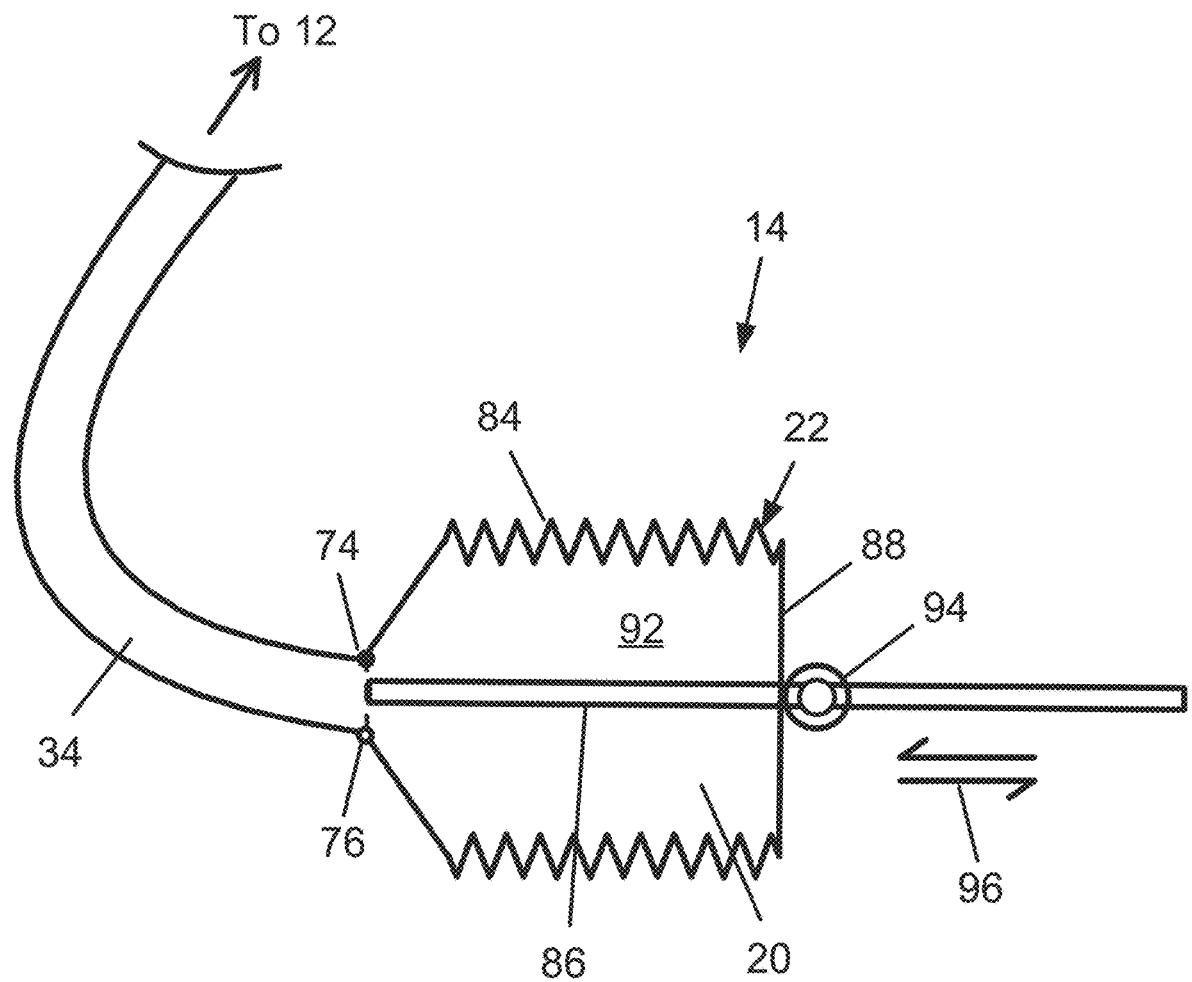

Turning now to FIGS. 8a and 8b, there is shown schematic block representation views of a portion of the TEPAP apparatus 10 according to yet another embodiment of the present disclosure, further for two of a plurality of different operational settings. The embodiment of FIGS. 8a and 8b are similar to the embodiment of FIGS. 1a, 1b, 7a and 7b, with the following differences. In particular, the pressure transition housing 22 comprises (i) a bellows shaped volume member 84 and (ii) an adjustable elastic member 86. The bellows shaped volume member 84 comprises a flexibility along at least one axis thereof which defines the enclosed volume 20.

The adjustable elastic member 86 extends through an end wall 88 of the pressure transition housing 22, between a first position (at a distal end of the elastic member) and a second position opposite the first position of the bellows shaped flexible volume member 84, near a proximal end of the elastic member The adjustable elastic member 86 is adjustable with respect to the enclosed volume between a first tension length (FIG. 8a) and a second tension length (FIG. 8b) for (a) adjusting the at least one fixed volume size between a first fixed volume size 90 and a second fixed volume size 92, different than the first fixed volume size, and/or (b) adjusting a compliance of the bellows shaped flexible volume member 84. The adjustment of the elastic member 86 is accomplished via a releasable clasp or clamp 94 in directions as indicated via arrows 96, with respect to the enclosed volume 20. Any number of fixed volume sizes may be obtained via discrete locations for displacement of the clasp 94 along the length of the elastic member 86.

According to another embodiment, a method of tuning expiration positive airway pressure comprises providing an entrainment valve 12 and tuning, via an inspiration-to-expiration pressure transition tuning module 14 fluidly coupled with a downstream outlet port 60 of the entrainment valve 12, an inspiration-to-expiration pressure transition of the breathing cycle. The entrainment valve 12 includes an entrainment valve housing 56 having an upstream inlet port 58, the downstream outlet port 60, and at least one valve 62. The at least one valve 62 is disposed within a wall of the entrainment valve housing 56 between the inlet port and the outlet port for (i) enabling inspiration airflow between an exterior of the entrainment valve housing and the inlet port during an inspiration breathing phase of a breath cycle and (ii) preventing expiration airflow between the inlet port and the exterior of the entrainment valve housing during an expiration breathing phase of the breath cycle. Tuning, via the inspiration-to-expiration pressure transition tuning module 14, includes facilitating at least one rate-of-change in pressure of the inspiration-to-expiration pressure transition that is non-instantaneous, wherein the at least one non-instantaneous rate of change in pressure is selected from among different non-instantaneous rates-of-change in pressure of the inspiration-to-expiration pressure transition.

In another embodiment, the method includes wherein the inspiration-to-expiration pressure transition tuning module 14 comprises an enclosed volume 20 within a pressure transition housing 22, and wherein the enclosed volume 20 is fluidly coupled to the entrainment valve outlet port 60. The enclosed volume 20 further includes at least a first portion having at least one fixed volume size for defining the at least one non-instantaneous rate-of-change in pressure of a transition from inspiration to expiration pressure.

As can be understood from this disclosure, the TEPAP apparatus comprises a supplemental device that drastically improves the comfort of EPAP by allowing a more gradual ramp up to expiratory pressures. Because air is compressible, dead space volume during EPAP has an effect on how the inspiratory pressures transition to the EPAP pressures. The larger the volume the longer the transition. Similarly, a smaller volume would have a shorter transition. In another embodiment, a method of TEPAP includes dynamically changing a resistance to exhalation by changing the non-anatomical dead space (i.e., the enclosed volume).

The TEPAP system can be tuned initially by patient or therapist based on sleep study prescription and appropriate comfort level. Additionally, the TEPAP system dead space can be dynamically adjusted for one or more of the following inputs:

1. Per sleep cycle every night:
   changed so low pressure/long ramp while falling asleep;
   changed to therapeutic pressures and ramp time during sleep; and
   changed based on a software input or simple kitchen timer.
2. Per prescription change from these inputs:
   follow-up sleep study after a period of time;
   SMART SLEEP™ or equivalent smart device for measuring sleep related metrics (i.e., brainwaves, patient flow, etc.); and
   CPAP, APAP, and BiPAP.

In regard to the above-mentioned inputs, a simple timer could be could also be added to increase EPAP over time. For example, if a user starts to wake up, the TEPAP system could possibly change to higher ramp time. In another example, although sleep apnea can occur during any stage of sleep, it is often worst during rapid eye movement (REM) sleep because of reduced muscle tone in the upper airway that naturally occurs during REM sleep. Some individuals, in fact, have apnea that only occurs during REM sleep. If this is linked to SMART SLEEP™, the system could be appropriately configured such that EPAP is applied only during the REM sleep cycle.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used, stand alone or in combination with other types of PAP (e.g., hybrid PAP) therapies and/or applications, to benefit a number of conditions, including obstructive sleep apnea (OSA); snoring; chronic obstructive pulmonary disease (COPD), bronchitis; asthma; heart failure; and hypertension. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A tuneable expiration positive airway pressure apparatus, comprising:
   (1) an entrainment valve including an entrainment valve housing having an upstream inlet port, a downstream outlet port, an opening defined in a wall of the housing between the inlet port and the outlet port communicating an interior of the housing to ambient air, and at least one valve disposed within a wall of the entrainment valve housing between the inlet port and the outlet port for selectively blocking or unblocking the opening (i) enabling inspiration airflow from ambient air into an interior of the housing by unblocking the opening during an inspiration breathing phase of a breath cycle and (ii) preventing expiration airflow from the interior of the housing to ambient air by blocking the opening during an expiration breathing phase of the breath cycle; and
   (2) an inspiration-to-expiration pressure transition tuning module comprising:
      (a) a pressure transition housing fluidly coupled to the entrainment valve outlet port such that gas existing the entrainment values enters an enclosed volume defined within the pressure transition housing, and,
      (b) a volume adjustment element that is selectively movable so as to change a size of the enclosed volume between a first fixed volume size and a second fixed volume size for tuning an inspiration-to-expiration pressure transition of the breath cycle, wherein tuning includes facilitating at least one rate-of-change in pressure of the inspiration-to-expiration pressure transition that is non-instantaneous, and wherein the at least one non-instantaneous rate of change in pressure is selected from among different non-instantaneous rates-of-change in pressure of the inspiration-to-expiration pressure transition based on the enclosed volume set by the volume adjustment element.

2. The apparatus according to claim 1, wherein the pressure transition housing is a cylindrical housing, and wherein the volume adjustment element comprises a piston disposed within the enclosed volume, wherein the piston is displaceable within that enclosed volume between at least a first position and a second position for changing the at least one fixed volume size between the first fixed volume size and the second fixed volume size, different than the first fixed volume size.

3. The apparatus according to claim 2, further comprising a resilient member coupled internal to the enclosed volume between the piston and an inner wall of the enclosed volume, wherein the resilient member is configured to adjust a compliance of the enclosed volume.

4. The apparatus according to claim 1, wherein the volume adjustment element comprises (i) a bellows shaped flexible member forming a portion of the pressure transition housing—and defining a boundary portion of the enclosed volume, and (ii) an elastic member moveably coupled with the pressure transition housing and displaceable with respect to the enclosed volume between at least a first position and a second position for (i) adjusting the at least one fixed volume size between the first fixed volume size and the second fixed volume size, different than the first fixed volume size, and/or (ii) adjusting a compliance of the bellows shaped flexible member.

5. The apparatus according to claim 1, wherein the pressure transition housing comprises (i) a bellows shaped volume member having flexibility along at least one axis thereof which defines the enclosed volume, and (ii) an adjustable elastic member extending between a first position and a second position opposite the first position of the bellows shaped flexible volume member, wherein the adjustable elastic member is adjustable with respect to the enclosed volume between a first tension length and a second tension length for (a) adjusting the at least one fixed volume size between the first fixed volume size and the second fixed volume size, different than the first fixed volume size, and/or (b) adjusting a compliance of the bellows shaped flexible volume member.

6. The apparatus according to claim 1, further comprising: a patient interface fluidly coupled to the entrainment valve via the inlet port.

7. The apparatus according to claim 6, further wherein the patient interface and the inspiration-to-expiration pressure transition tuning module are integrally formed.

8. The apparatus according to claim 1, further comprising: a hose fluidly coupled between (i) the entrainment valve outlet port and (ii) the enclosed volume within the pressure transition housing.

9. The apparatus according to claim 8, further wherein the hose and the inspiration-to-expiration pressure transition tuning module are integrally formed.

10. A method of tuning expiration positive airway pressure, comprising:
providing an entrainment valve that includes an entrainment valve housing having an upstream inlet port, a downstream outlet port, an opening defined in a wall of the housing between the inlet port and the outlet port communicating an interior of the housing to ambient air, and at least one valve disposed within a wall of the entrainment valve housing between the inlet port and the outlet port for selectively blocking or unblocking the opening (i) enabling inspiration airflow from ambient air into an interior of the housing by unblocking the opening during an inspiration breathing phase of a breath cycle and (ii) preventing expiration airflow from the interior of the housing to ambient air by blocking the opening during an expiration breathing phase of the breath cycle; and
providing an inspiration-to-expiration tuning module comprising: (a) a pressure transition housing fluidly coupled to the entrainment valve outlet port such that gas existing the entrainment values enters an enclosed volume defined within the pressure transition housing, and, (b) a volume adjustment element that is selectively movable so as to change a size of the enclosed volume between a first fixed volume size and a second fixed volume size,
tuning, via the inspiration-to-expiration pressure transition tuning by changing the enclosed volume using the volume adjustment element, an inspiration-to-expiration pressure transition of the breath cycle, wherein tuning includes facilitating at least one rate-of-change in pressure of the inspiration-to-expiration pressure transition that is non-instantaneous, wherein the at least one non-instantaneous rate of change in pressure is selected from among different non-instantaneous rates-of-change in pressure of the inspiration-to-expiration pressure transition.

11. The method according to claim 1, wherein the pressure transition housing comprises is a cylindrical housing, and wherein the volume adjustment element inspiration-to-expiration pressure transition tuning module further comprises a piston disposed within the enclosed volume, wherein the piston is displaceable within that enclosed volume between at least a first position and a second position for changing the at least one fixed volume size between the first fixed volume size and the second fixed volume size, different than the first fixed volume size.

12. The method according to claim 11, further comprising coupling a resilient member internal to the enclosed volume between the piston and an inner wall of the enclosed volume, wherein the resilient member is configured to adjust a compliance of the enclosed volume.

13. The method according to claim 1, wherein the pressure transition housing comprises (i) a bellows shaped flexible member forming a portion of the pressure transition housing and defining a boundary portion of the enclosed volume, and (ii) an elastic member displaceable with respect to the enclosed volume between at least a first position and a second position for (i) adjusting the at least one fixed volume size between the first fixed volume size and the second fixed volume size, different than the first fixed volume size, and/or (ii) adjusting a compliance of the bellows shaped flexible member.

14. The method according to claim 1, wherein the pressure transition housing comprises (i) a bellows shaped volume member having flexibility along at least one axis thereof which defines the enclosed volume, and (ii) an adjustable elastic member extending between a first position and a second position opposite the first position of the bellows shaped flexible volume member, wherein the adjustable elastic member is adjustable with respect to the enclosed volume between a first tension length and a second tension length for (a) adjusting the at least one fixed volume size between @the first fixed volume size and the second fixed volume size, different than the first fixed volume size, and/or (b) adjusting a compliance of the bellows shaped flexible volume member.

15. The method according to claim 10, further comprising: fluidly coupling a patient interface to the entrainment valve via the inlet port.

* * * * *